United States Patent [19]

Karz

[11] 4,173,971
[45] Nov. 13, 1979

[54] CONTINUOUS ELECTROCARDIOGRAM MONITORING METHOD AND SYSTEM FOR CARDIAC PATIENTS

[76] Inventor: Allen E. Karz, 16820 Chatsworth St., Granada Hills, Calif. 91344

[21] Appl. No.: 828,368

[22] Filed: Aug. 29, 1977

[51] Int. Cl.² ............................................. A61B 5/04
[52] U.S. Cl. ................................... 128/702; 128/711; 128/904
[58] Field of Search ..................... 128/2.06 A, 2.06 B, 128/2.06 G, 2.06 R, 2.1 A; 346/33 ME

[56] References Cited

U.S. PATENT DOCUMENTS

| | | |
|---|---|---|
| 3,593,705 | 7/1971 | Thomas et al. ................. 128/2.06 A |
| 3,648,689 | 3/1972 | Dominy .......................... 128/2.06 R |
| 3,726,270 | 4/1973 | Griffis et al. ..................... 128/2.1 A |
| 3,779,237 | 12/1973 | Goeltz et al. .................. 128/2.06 A |
| 3,799,148 | 3/1974 | Rower ............................ 128/2.06 A |
| 3,885,552 | 5/1975 | Kennedy ......................... 128/2.1 A |
| 3,934,267 | 1/1976 | Kosaka et al. .................. 128/2.06 G |

*Primary Examiner*—William E. Kamm
*Attorney, Agent, or Firm*—Nilsson, Robbins, Dalgarn, Berliner, Carson & Wurst

[57] ABSTRACT

A system which is capable of allowing an attending physician to continuously monitor the electrocardiogram (ECG) signals produced by a cardiac patient. The signals, generated by the patient, are first recorded in real time over a predetermined time period established by the physician. At the conclusion of the predetermined time period a monitoring station is automatically alerted by telephone and commences receiving the patient's real time ECG signals directly. The recorded ECG signals are then transmitted in a compressed time fashion to the monitoring station simultaneously with the real time ECG signals. The monitoring station receives the compressed time and the real time transmitted signals and following analysis thereof transmits a report of selected portions of the ECG to the physician. Upon instructions from the physician, the monitoring station either returns the recording apparatus to its normal operational status for a predetermined time period, or continues to receive and analyze the real time ECG signal until the patient's signal is sufficiently stable and then returns the recording apparatus to its normal operational status. This process repeats continuously. The physician communicates directly with the monitoring station and with the patient as may be required. The system and method provides close and complete monitoring of the patient with complete ECG data retrieval and individualized close patient surveillance.

38 Claims, 10 Drawing Figures

CONTINUOUS ELECTROCARDIOGRAM MONITORING METHOD AND SYSTEM FOR CARDIAC PATIENTS

BACKGROUND OF THE INVENTION

It has been recognized by physicians that it is extremely important to continuously monitor cardiac patients immediately following coronary attacks. Such is normally accomplished very effectively in the coronary care unit of most American hospitals where the patients are continuously monitored following heart attacks to detect arrhythmias of the heart, particularly warning ventricular arrhythmias which may lead to ventricular fibrillation and death. Through prompt recognition and treatment of these warning ventricular arrhythmias in coronary care units, the mortality rate of acute myocardial infarctions has been reduced by one half. In addition, approximately 15% of post myocardial infarction cardiac patients continue to have frequent ventricular extra systoles (more than 20 per hour) after discharge from the hospital and while in an out-patient status.

This experience has led physicians to the recognition that it is desirable to continue such direct intensive monitoring of the high risk cardiac patient's ECG signals subsequent to release from the cardiac care unit. Constant monitoring of these patients after release from the hospital is difficult because of the logistics involved and particularly since they can no longer be monitored closely as a group by direct wiring or close telemetry such as is possible in a hospital. As a result, various systems have been developed to attempt to monitor the ECG signals of out-patients to thereby provide a diagnostic tool for additional treatment or variation of treatment for the patients as may be required.

The systems currently in existence for such out-patient ECG signal monitoring basically fall into four main types, which are, portable tape recorders, telephone transmission devices, radio transmission devices, and tape recorders which use telephone transmission. While each of these devices operates quite well, there are in each of the systems disadvantages and limitations which preclude safe, close and continuous monitoring of the ECG signals generated by the out-patient. Since the warning ventricular arrhythmias which lead to ventricular fibrillation may develop at any time and without prior indication and, in fact, sometimes without the patient even recognizing such is occurring, that is, no physical symptoms are immediately present, it is apparent that the patient may expire during the time when the cardiac signals are being recorded but are not to be soon reviewed.

The typical portable tape recorder systems currently in existence must be worn continuously by the patient for the period of time for which they are designed to record typically 12 to 26 hours. The device weighs from one to two pounds and thus is relatively heavy and uncomfortable to the patient. Subsequent to the time during which recording occurs, the recorder is returned to the medical facility by the patient where the tape can be removed and the device can be placed in condition for a new recording. The recorded tape is then analyzed and a report thereon is transmitted to the attending physician who can then decide further activity or treatment as may be required. Obviously, such devices result in a delayed data retrieval and analysis in that the tapes are returned only subsequent to the predetermined recording period (between 12 and 26 hours). In addition, there is a further delay while the patient returns the tape recorder to the scanning facility, the scanning facility analyzes the recording, compiles a report and transmits it to the physician. Thus, during the time when recording ceases and until the tape is removed, no recordation of the ECG signal is being made. As can also be seen, these devices have a severe distance limitation in that the recording must be scanned at a specialized medical facility and thus is impractical for patients who live long distances from such facility.

As further evidence of the limitations of these devices reference is made to the January, 1977 issue of Circulation, An Official Journal of the American Heart Association, Inc., Volume 55, No. 1, page 210 and 211; and to the May 26, 1977 issue of The American Journal of Cardiology Volume 39, pages 873-879; and to the May 1972 issue of Archives of Internal Medicine, Volume 129, pages 773-779. These three articles report deaths occurring from ventricular fibrillation while the patient was wearing a tape recorder.

Some of the telephone transmission devices are designed in such a way that they will automatically detect a warning arrhythmia and sound an alarm to thereby alert the patient. The patient is then expected to telephone the medical facility to transmit the ECG signals which have been converted to a frequency modulated signal within the audio range of the telephone. Some of the devices do not have an automatic arrhythmia detection system but instead depend upon the patient recognizing a symptom such as palpitations, chest pain, shortness of breath or lightheadedness which may be caused by the warning arrhythmia. If the patient recognizes the symptom, the patient then dials the medical facility and transmits the signal by telephone. These telephone transmitting devices have a number of shortcomings. It is obvious that the warning arrhythmias causing the symptoms or the automatic alert to occur are missed because the medical facility can only begin to record once the patient has completed the call. Thus the medical facility only begins to record subsequent to the occurrence of such warning arrhythmias. It is obviously also impractical for the patient to maintain the telephone contact with the medical facility for longer than a few minutes time during which the patient must remain by the telephone. Thus only a very small amount of ECG signal data is, in fact, ever received or recorded by the medical facility. As above noted often a patient will not recognize the symptoms of a warning arrhythmia and thus this warning arrhythmia may never be recorded. In addition the patient may be incapacitated by the arrhythmia or already unconscious and thus is unable to complete a telephone call and may expire prior to any data being transmitted to the medical facility. Furthermore, if the patient's ECG signals are to be transmitted for any substantial period of time the telephone lines at the patient's home and the medical facility may be tied up for substantial periods which adds to inconveniences as well as tremendous expense.

The radio transmission devices again operate upon the principle of detecting arrhythmias through the use of electronic logic networks. When such occurs the radio transmission capability is actuated and the ECG signals are transmitted through the use of a UHF or VHF radio transmission to a central medical facility capable of recording and analyzing the signals. Obviously, these devices suffer from distance limitations in that the radio transmissions are typically line of sight and may also have tremendous reliability problems in that the UHF and VHF signals may be disturbed as a result of concrete-steel construction which may exist between the patient and the central receiving facility. There are also only a limited number of radio channels allotted to this type of transmission which automatically limits the number of patients capable of being monitored within the receiving range of any medical facility. Furthermore, the problem with respect to incomplete data retrieval as above-described is also inherent in a system of this type. In addition, the radio transmission devices as well as the telephone transmission devices which have the automatic detection systems therein, suffer from the additional problem in that the signals which cause the activities of the system are typically warning arrhythmias. These devices allow no way to quantitate total heartbeats or to detect trends which reflect the rate or QRS morphology changes. These latter provide information supplemental to the detection of arrhythmias which information is significant to a physician treating a high-risk cardiac out-patient. Furthermore, there is no way to tell what warning arrhythmias are not being detected by the electronic logic in the radio transmission devices and, in fact, significant arrhythmias may be missed which cannot be verified because only limited portions of the ECG signal are being retrieved.

Where the portable tape recorder is utilized along with the telephone transmitter system, one can immediately ascertain that the incomplete data retrieval above referred to exists in addition to the tying up of telephone lines both at the patient's home and at the medical facility. In addition thereto, one skilled in the art will recognize that by continuously recording, rewinding and replaying the recorded information on the tape less than one-half of the patient's ECG signal history is being recorded and transmitted. If the patient is required to frequently record and play back, for example, in ten minute intervals, it will immediately also be seen that the patient is constantly calling the medical facility every 20 minutes to transmit his 10 minute recorded signal. Such would mean that he would be telephoning the medical facility approximately 72 times through a 24 hour period which, obviously, becomes impractical for a high-risk cardiac out-patient.

The best prior art known to applicant is described in the following U.S. Pat. Nos. 3,199,508; 3,212,496; 3,267,934; 3,434,151; 3,603,881; 3,650,263; 3,724,455; 3,742,938; 3,768,017; 3,779,237; 3,832,994; 3,639,907; 3,880,144; 3,882,277; 3,893,453; 3,972,320; 3,910,260; 3,934,267; 3,946,744; 3,951,135; 3,958,563; 3,986,498; 3,991,747; 3,913,567.

SUMMARY OF THE INVENTION

A system for continuously monitoring ECG signals from a patient comprising means for recording atrial and ventricular ECG signals in real time at a predetermined rate along with means for reproducing the prerecorded signals at a different rate which is greater than the rate at which the signals were recorded so as to compress the time required to reproduce the signals as compared to the time required to originally record the signals. Means for monitoring the reproduced signals is connected through a communications interface with the means for reproducing the signals thereby to enable a qualified person to analyze the signals and provide appropriate care for the patient.

A method for continuously monitoring ECG signals from a patient including recording atrial and ventricular ECG signals in real time at a predetermined rate and reproducing the prerecorded signals at a different and greater rate so as to compress the time required to reproduce the signals as compared to the time required to originally record the signals, monitoring and analyzing the reproduced signals and providing treatment for the patient responsive to the information on the reproduced signals.

DETAILED DESCRIPTION

Figure 1:
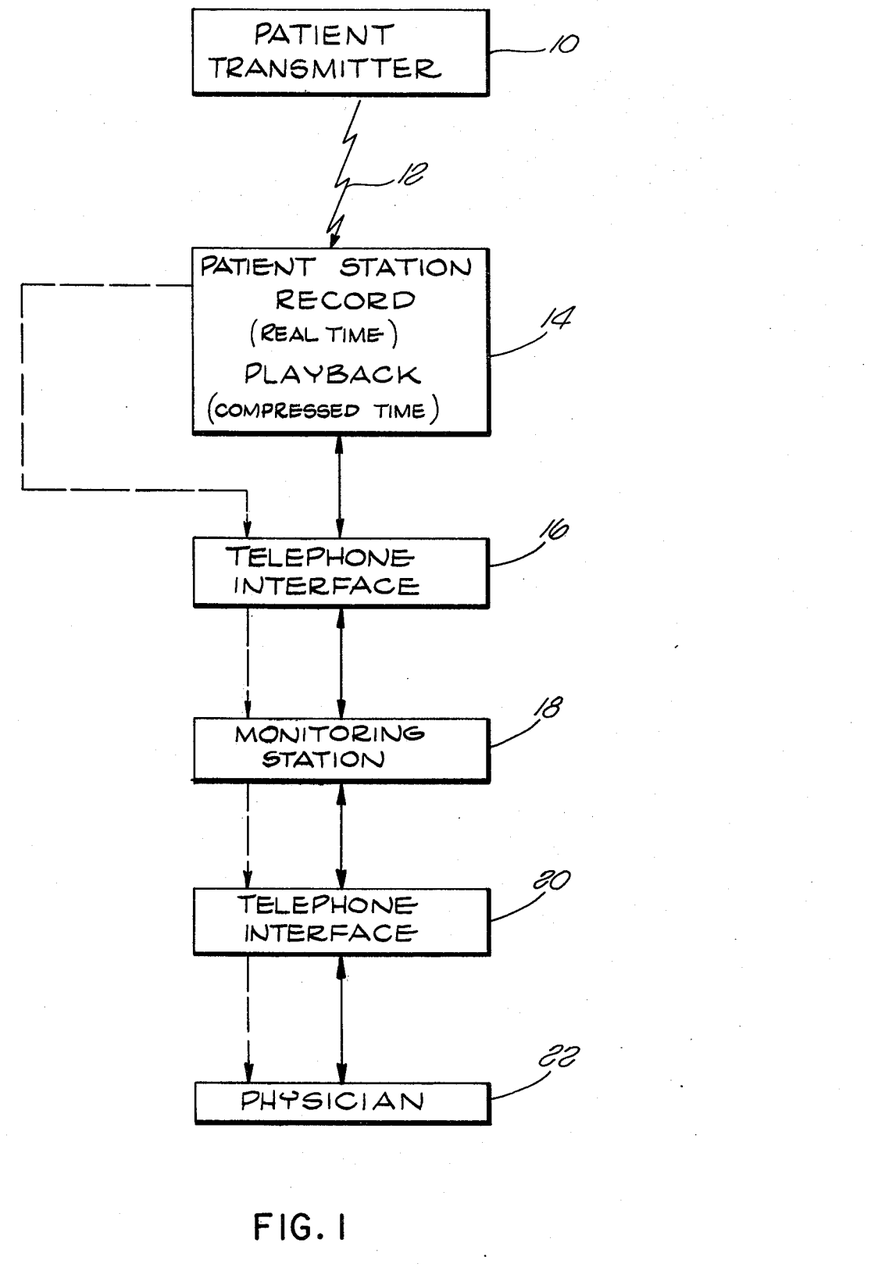
FIG. 1 is a block diagram generally illustrating the continuous monitoring system for cardiac patients constructed in accordance with the present invention.

As is illustrated in FIG. 1, to which reference is hereby made, a system constructed in accordance with the present invention, includes a patient transmitter 10 which may be worn at all times by a patient who is under cardiac care. The patient transmitter includes a state of the art telemetry transmitter apparatus which may transmit ECG signals as indicated by the communication link 12 to a patient station which is in the form of a portable console or similar apparatus. Obviously, other physiological signals such as blood pressure, pulse rate, respiratory rate and the like may also be transmitted if desired and would be useful to the attending physician. For ease of illustration and clarity of description, only ECG signals will be referred to throughout but it is intended to include other physiological signals as well. It should also be understood that the patient's station may be powered by plugging into the standard wall electric outlet or alternatively may be battery powered. Thus the patient's station may be carried by the patient such as between work and home or the like and maintain continuous recording of the ECG signals. The patient station 14 includes means to record, in real time, the ECG signals developed by a patient. In addition thereto, the patient station also includes means for reproducing or playing back the prerecorded ECG signals in a substantially compressed time as compared to the real time required to record the signal. A telephone interface 16 is connected between the patient station 14 and a monitoring station 18. Through the utilization of appropriate control means the telephone instrument is activated to provide both the compressed time reproduced signals (as illustrated by the solid lines between the blocks) as well as the real time signals (as illustrated by the dashed lines between the blocks) directly to the monitoring station 18. As a result, the patient's ECG signals both real time and prerecorded are being monitored at the monitoring station 18.

After analysis of the ECG signal being received selected portions thereof are transmitted to the physician for his review. An additional telephone interface 20 is provided to permit direct communication between the monitoring station and the physician 22. In the event such may be required, the physician can communicate not only with the monitoring station but also with the patient as is illustrated by the arrows at each end of the lines between the blocks 14-22. Through these lines either the physician or the monitoring station, upon orders of the physician, may communicate to the patient or to the patient station any desired and detailed information, depending upon the outcome of the analysis of the ECG signals received from the patient both as a result of the reproduced and real time signals being received. It will be recognized by those skilled in the art that a system constructed in accordance with the present invention which provides a continuous monitoring of ECG signals may be utilized in various ways. Obviously, one of these ways is to monitor cardiac outpatients during the approximately six month period subsequent to release from a hospital during which they are most susceptible to ventricular fibrillation and other lethal arrhythmias and as a result thereof, expiration. In addition thereto, such patients normally are under medication or exercise programs or a combination of both, and in many instances have undergone aorto-coronary saphenous vein bypass graft surgery. Little is known at the present time regarding the exact effects of exercise, medicines and surgery upon ventricular arrhythmias. Long range investigation, study and analysis is required to provide the data which will result in better utilization of drugs, exercise and surgery in treating cardiac patients. An apparatus constructed as is the system of the present invention will definitely provide this immediate capability since it is extremely simple, lightweight, easy to use and requires little or no direct involvement of the patient other than the wearing of the electrodes and the lightweight telemetry transmitter.

In addition, a continuous monitoring apparatus constructed in accordance with the present invention may also be utilized in intensive care coronary units in modern hospitals for the purpose of permitting the patient's ECG signals to be applied to a computer properly programmed to analyze the same for quantitation of arrhythmias and the like. At the present time only a very small percentage of coronary care units throughout the country utilize computers because of the large expense involved for the purchase of computers. The system of the present invention alleviates this problem because the patient's ECG signals may be transmitted directly to a central computer serving multiple hospitals with a summary report being transmitted to the coronary care unit from this central computer. The several patients in each coronary care unit would have their prerecorded time compressed and real time ECG signals transmitted serially over a single telephone line. The monitoring technician would coordinate and cycle these transmissions. Thus one computer managed by one monitoring technician can follow multiple patients from multiple coronary care units with minor expense for each of the coronary care units involved. Similarly, rest and convalescent homes where many of the elderly patients are subject to coronary disease and arrhythmias may utilize this system with minimal equipment to the great benefit of the patients involved.

As above pointed out, when a patient is on an exercise program of some type such as utilization of a stationary bicycle or jogging in place for set periods of time and/or at set workloads, the apparatus of the present invention may be worn thus providing ECG signals to the monitoring station. From analysis of these ECG signals it can be detected if arrhythmias increase, decrease, or remain the same as a result of such exercise programs and thus whether medication or treatment should be undertaken or modified. Similarly, some cardiac patients have arrhythmias but at very infrequent times. It is extremely important with respect to such patients that they be continuously monitored to detect these infrequent arrhythmias. By the continuous monitoring of the present system, such infrequent arrhythmias occurring even, for example, such as once per week or twice per month may be detected simply because the patient's ECG signals are being continuously monitored and the technician and/or computer will detect such arrhythmias when they are transmitted. In addition, the continuous monitoring capability of the system of the present invention may also be useful in detecting rare malfunctions occurring in a permanent pacemaker worn by a patient. The only way to detect and repair such malfunctions is to monitor the patient until the malfunction occurs and is reflected in the ECG.

Figure 2:
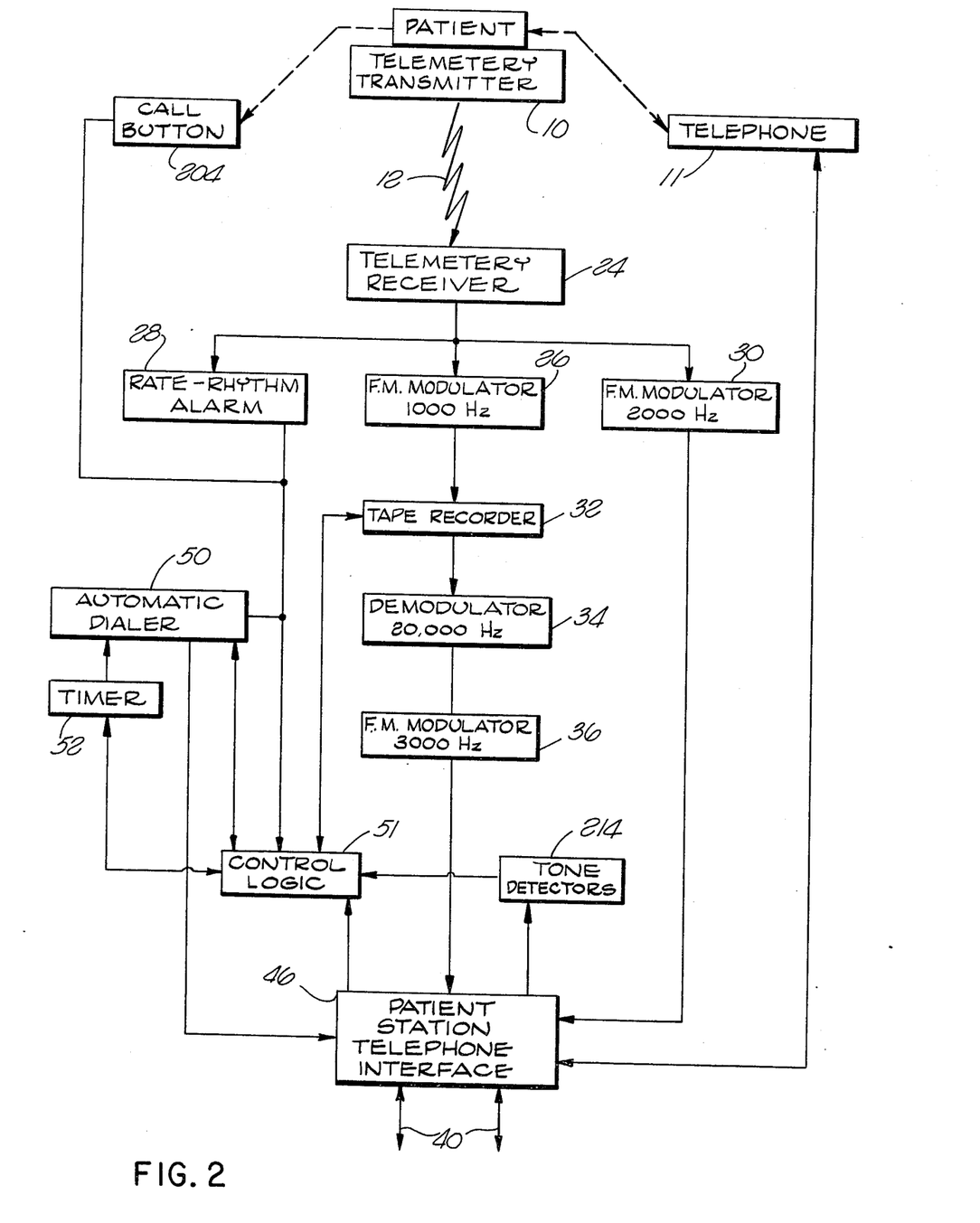
FIG. 2 is a block diagram showing in more detailed form the patient station of the system.

Referring now more particularly to FIG. 2, the patient station 14 is shown in somewhat more detail. As is therein illustrated, a telemetry receiver 24 receives the signal transmitted from the telemetry transmitter 10. The signal received by the telemetry receiver is applied to a F.M. modulator 26 which frequency modulates the received signals about a 1000 hertz center frequency. The signals are also applied simultaneously to a rate-rhythm alarm 28 which will be discussed more in detail below. The output signals from the modulator 26 are applied to a tape recorder 32. The tape recorder has a record mode wherein the signals applied thereto are recorded in real time at a first predetermined rate of recording such, for example, as 15/16 inches of tape per second. When the predetermined time period during which recording occurs expires and communication with the monitor station has been established, an appropriate control circuit will stop the recording, rewind the tape rapidly, and then cause the tape to play back at a very rapid speed as compared to the original recording speed, for example, at 18.75 inches of tape per second (20 times faster than the recording speed). Thus the time required for reproducing the signals recorded upon the tape is compressed substantially as compared to the original time of recording of said signals. When the compressed time playback has been completed and the end of the tape or a signal from the monitor station is received indicating that the time required for the playback has expired, whichever occurs first, the tape is then again caused to rewind at a rapid speed and the system is returned to a record mode to record the signal received from the patient in real time. As will be obvious to those skilled in the art it is not necessary that the tape be rewound at each point in order to accomplish the reproduction of the signals prerecorded thereon at the compressed time. For example, a continuous tape may be provided in cassette or reel to reel form with appropriate cue marks appearing thereon. When the appropriate cue marks arrive at the record head, appropriate control circuits can be energized which will place the tape recorder and associated equipment 32 into the playback at compressed time mode thus causing the signals to be immediately transmitted at the compressed time unit until an additional cue mark is received at which point in time the tape transport is again returned to a record in real time mode. Obviously, the tape may be played back at an increased speed in a reverse direction if desired.

The signals received by the receiver 24 are also applied to a F.M. modulator 30 which is connected directly to the telephone interface 46. During the time the tape recorder is not recording the patient's ECG signals they are being transmitted directly over the telephone in real time to the monitor station.

During the time that the prerecorded signals are played back in compressed time, the signals thus reproduced are applied to a demodulator 34 which operates at the approximate multiple of the recording center frequency (e.g., 20 times) such as at a 20,000 hertz center frequency. Such is required since the original signal from the telemetry receiver is F.M. modulated at a 1000 hertz center frequency and has now been increased to 20,000 hertz by the 20 times record speed playback. An additional modulator 36 is coupled to the demodulator 34 to modulate the resulting signal at 3000 hertz center frequency which is within the passband required for transmission over the telephone line. This signal is then applied through the patient's station telephone interface 46 for transmission over the telephone line 40 to the monitoring station 18.

As is noted, the phone dialer 50 has connected thereto a timer 52. The timer controls the point at which the system dials the monitoring station. The timer 52 may be set or reset by the monitor technician through the control logic to any desired time period at the direction of the physician to control the periodicity of the contact with the monitor station and thence the rewinding and playback of the signals being recorded by the tape recorder 32.

An indicated, the signal from the telemetry receiver is also applied to the rate-rhythm alarm 28. In the event that the patient's real time received ECG signals deviate from a predetermined pattern, thus indicating the occurrence of a severe bradycardia, or severe tachycardia, or a dangerous arrhythmia (e.g. more than five ventricular ectopic beats (VEB) per minute), the rate-rhythm alarm will detect such and through the control logic 51 will automatically activate the phone dialer 50 which, through the utilization of the distance direct dialing techniques currently available, through the patient station's telephone interface 46, immediately alerts the monitoring station 18 which will commence to receive the real time ECG signal over the telephone line 40.

From a consideration of the block diagram as shown in FIG. 2, it will be recognized by those skilled in the art that the patient generating the ECG signals is constantly being monitored by the recording equipment 32 and/or the monitoring station 18. Through the utilization of the timer 52, the patient's real time signals being recorded can be replayed at any interval desired by the physician from a few minutes to hours as the case may be depending upon the history of the patient at that particular point in time. This occurs without the patient being aware of any changes that may have taken place. The only requirement of the patient is that he maintain himself in a position such that the telemetry transmitter 10 and the telemetry receiver 24 remain in radio contact at all times. Typically such transmitters have a very effective range of approximately 500 feet depending upon the particular local conditions, thereby providing ample movement by the patient in his normal day to day activities, either at home or at work. A call button 204 may be used by the patient to activate the telephone 11 as will be explained more fully below. A tone detector or monitor 214 is used for control purposes as will also be more fully explained below.

Figure 3:
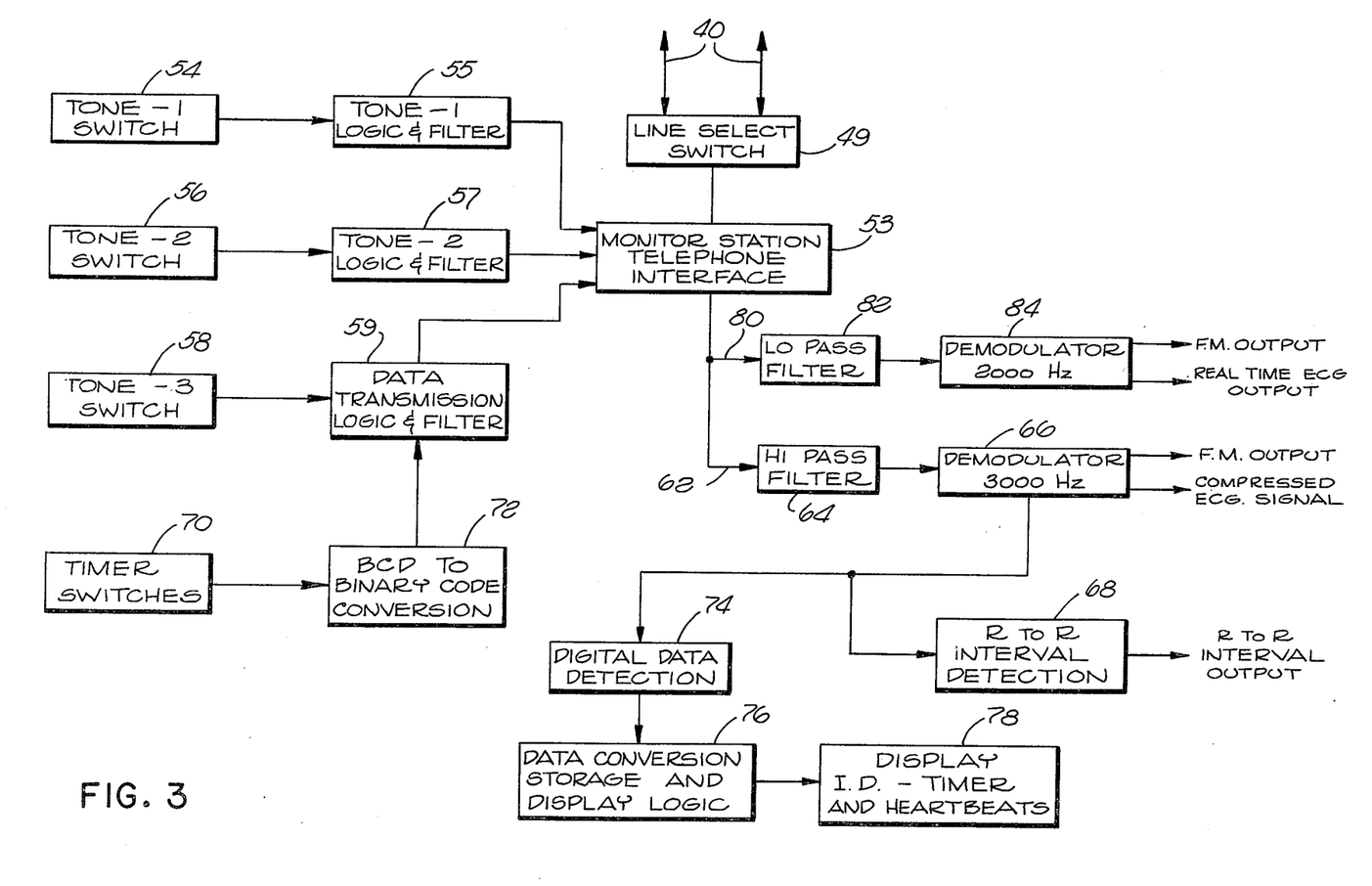
FIG. 3 is a block diagram showing in more detailed form the monitor station.

Referring now more particularly to FIG. 3, the monitor station 18 is shown in further detail. As is therein shown the signals on the telephone line are passed through a line select switch 49 and to the monitor station telephone interface 53. The compressed time signal is applied by way of a connection 62 to a high pass filter 64 and from there to a demodulator 66 at 3,000 hertz center frequency to thus develop a first signal which is representative of the compressed time signal, in accordance with the present example at 20 times the recorded real time signal. This reproduced compressed time signal may be applied to any device desired to assist the technician at the monitor station in analysis of the signal. For example, this signal may be applied to a computer, an oscilloscope, a strip chart recorder, a tape recorder or a combination of all of these.

The signal from the patient's station which is transmitted in real time is coupled over the line 80 to a low pass filter 82 and to a demodulator 84 at 2000 hertz which in turn produces a real time signal. The real time signal likewise may be applied to the computer, oscilloscope, strip chart recorder, tape recorder or any combination thereof as again may be required to assist the technician in his task. The monitor technician receives the information from the various recording and/or readout devices and analyzes the same. The monitoring technician may generate a desired tone signal as indicated by the tone-1 switch 54, tone-2 switch 56 and tone-3 switch 58. Such switches activate appropriate logic as illustrated at 55, 57 and 59, respectively. Timer switches 70 are used by the monitor technician to set or reset the timer 52 at the patient's station. Upon setting the switch 70, appropriate control signals are generated at 72 and are applied to the data transmission logic 59 and over the telephone line through the control logic 51 to the timer 52. Likewise the tone signals are applied through the monitor station telephone interface 53 to the patient's station for purposes as will be described more fully hereinafter.

The output signals from the demodulator 66 are also applied to a rate-rhythm (RTOR) interval detection device 68 which produces an output signal indicative of any changes in the pulse rate or rhythm thereof of the patient. The signal is also applied to a digital data detection means 74 which along with the conversion and display logic means 76 and display 78 provides patient identification and specific information regarding the patients such as total heartbeats; total VEB's, timer setting and the like.

The monitor technician may also provide a summary report with particular rate-rhythm samples to the physician by way of the telephone interface 20 (FIG. 1) and by way of utilization of communication methods that may be available to him such, for example, as a telephone copying apparatus. The physician reviews the transmitted information and if required, contacts the patient directly by voice communication. If desired, the physician may direct that there by a change in the setting of the timer 52 to a different recording period as may be indicated from the samples provided by the monitoring technician. As will also be recognized to those skilled in the art, the monitor technician may directly contact the physician (if he is not present) and alert the physician as to any difficulties which immediately appear to the monitor technician so that the physician may immediately contact the patient for consultation or instruction and obtain also the real time ECG signals for purposes of direct analysis thereof.

Figure 4:
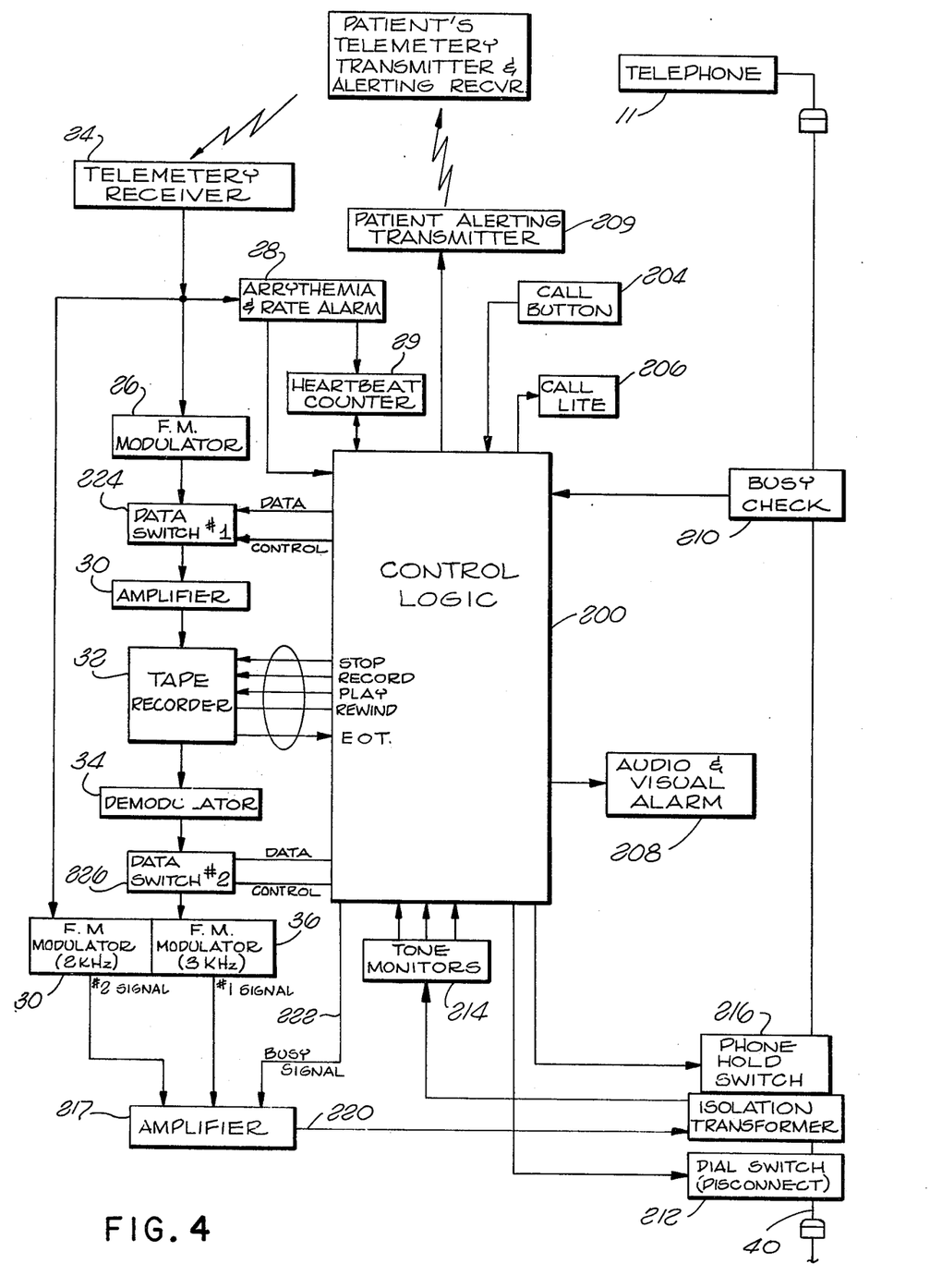
FIG. 4 is a block diagram showing the patient station of the system in yet further detail.

By now referring to FIG. 4, a more detailed block diagram of the patient's station 14 is illustrated. As is therein shown the control logic module 200 is interconnected with various additional portions of the patient's station. Functions of the control logic module will be discussed in more detail hereinafter. It will, however, be noted that the tape recorder 32 is connected through the cable 202 to the control logic module in such a manner that the control logic module can provide signals to stop, record, play and rewind the tape and additionally, the tape deck can provide a signal to the control logic module indicating that the end of the tape has been reached (EOT).

A call button 204 is interconnected also to the control logic module 200 and is utlized by the patient should such be required to automatically dial the monitoring station 18 simply by depressing the call button 204. Such may be required in the event the patient is experiencing symptoms which require immediate attention by the monitor technician or by the physician. An appropriate call light 206 is also interconnected with the control logic module and provides the patient with a means to determine whether the system is using the telephone line.

In the event the doctor or the monitoring station wish to alert the patient and to have him communicate by voice over the telephone there is provided an audible alarm and light 208 which is connected with the control logic module. Thus, in the event the doctor or monitor technician activates the system appropriately (Tone-2) a sound will occur that should alert the patient to immediately lift up his telephone and talk with the doctor and additionally a light will flash on and off to visually indicate that such should be done. Additionally, a patient alert transmitter 209 is provided to a signal the patient by radio transmission in the event he is remote from the patient station.

A busy check and disconnect apparatus 210 and 212 are interconnected between the telephone apparatus 11 and the control logic module 200 for purposes to be described more fully hereinafter. Basically, this permits the system to determine whether the telephone is being used for other purposes, for example, the patient is talking to someone and, if so, after an appropriate wait, and a warning signal, to disconnect the same, in order to dial the monitor station.

Tone detectors or monitors 214 are also interconnected with the system and receive appropriate indications confirming occurrences within the system as will be more fully described below.

Also provided is an appropriate switch and isolation means 216 which is interconnected between the control logic module and the telephone line to accomplish the appropriate switching of the signals as generated onto the telephone lines and to operate the phone system appropriately.

F.M. modulator 30 is connected to receive the real time signals from the receiver 24. The F.M. modulator 30 has a center frequency of 2000 hertz. This real time signal and in addition thereto, the compressed time signals which have been modulated by the F.M. modulator 36, are coupled through the amplifier 217, the line 220, and the switch and isolation means 216 to the telephone line. An appropriate busy signal may be applied from the control logic module by way of the connection 222 as an input to the amplifier 217 also thus providing an indication that the telephone will be busy. Appropriate switches 224 and 226 are incorporated between the signals and the control logic module 200 to provide appropriate activation such as selection of the signals or insertion of digital data for recording and/or transmission as will be more fully described below.

Figure 5:
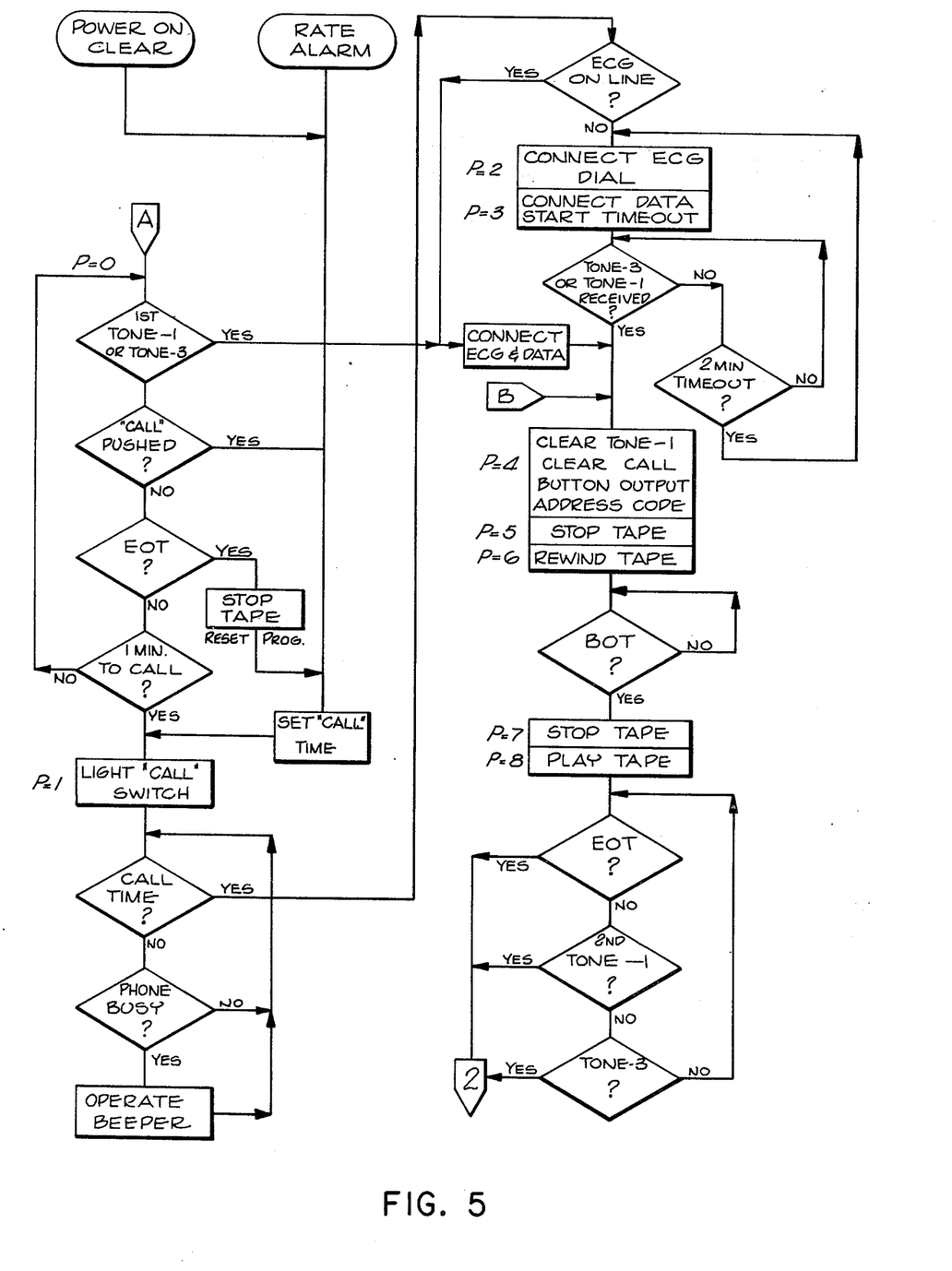
FIGS. 5, 6 and 7 are flow charts illustrative of the various operational steps within the system.
Figure 6:
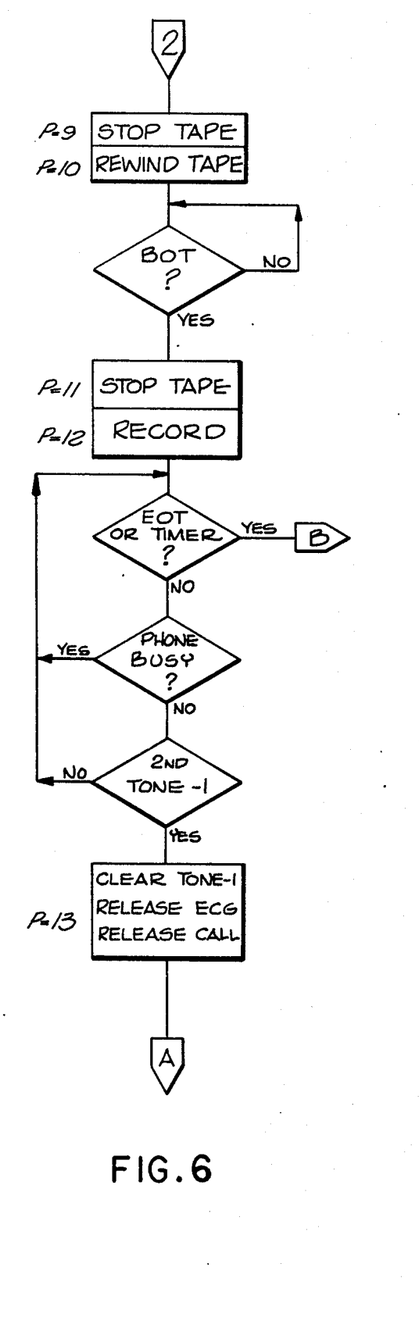
Figure 7:
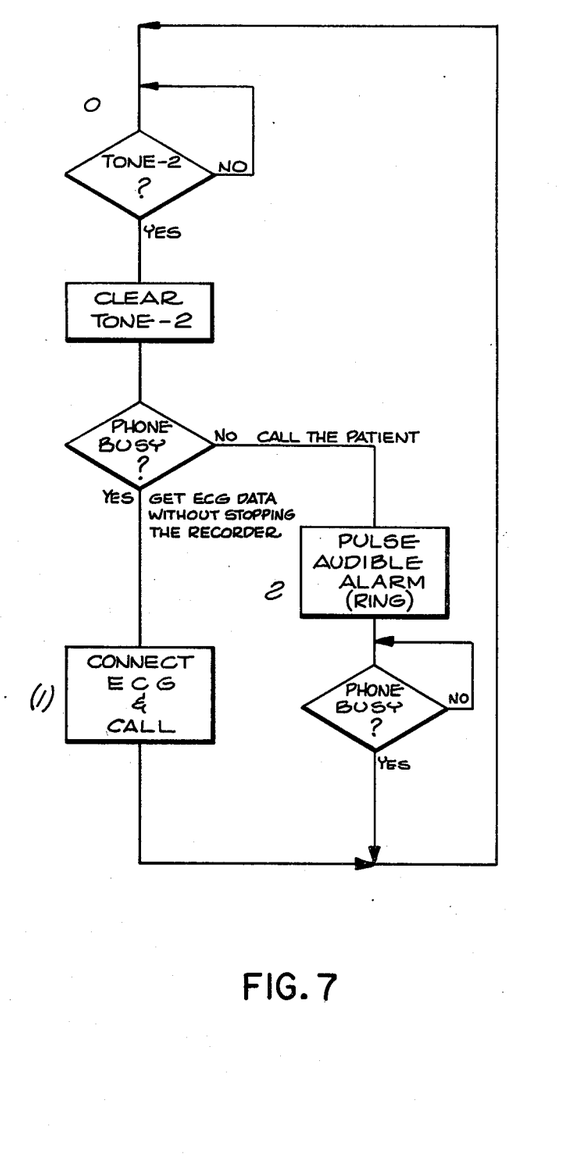

Referring now to FIGS. 5, 6 and 7, there is presented a flow chart indicating the various functional operations which occur within the patient's station at appropriate times. These times have been broken into various increments and identified as P0 through P13 each of which will be discussed individually below.

When the system is plugged in to an appropriate electrical outlet and into the four prong telephone jack or other telephone standard connectors normally provided, the power switch is first turned on which permits the entire system to clear and the logic to reset. Certain portions of the logic are set causing the system to dial the monitoring station for initial contact or to re-establish contact after an inadvertent power loss. At this point in time, the rate-rhythm alarm is activated and may commence operation at any time in the event of receipt of abnormal arrhythmias as above-described.

The first step is at P0. During P0 the telephone is available to the patient, the tape recorder is operating and is recording the real time signal upon the tape, there has been no rate-rhythm alarm signal indicating an abnormal arrhythmia requiring immediate attention and the patient's telemetry transmitter is working properly. During this period of time any one of four things may occur. A tone 1 or tone 3 may be received. In the event one of these tones occurs, it indicates that either the doctor has called the patient and wishes him to respond or alternatively, the patient has called the doctor (through or at the monitor station) and wishes to communicate as a result of some problem. The doctor or monitor technician by activating the appropriate tone, can, in fact, cause the equipment to connect to the telephone line without any assistance from the patient. The second thing which may occur is that the call button may be activated as a result of the patient or his agent having pushed the same. Such will cause a call to the monitor station and/or doctor. Automatically the same thing would occur in the event of a rate-rhythm alarm or a power-on-clear signal having occurred indicating that the power was off and came on again. In addition to the above two items, there may also occur an end of tape signal. If such occurs it means that the tape has run out and if that does occur, the tape is stopped thus avoiding any damage to the tape transport equipment. Such also activates the dialing and causes the monitor station to be called.

The fourth thing that may happen during P0 is that the timer runs to within one minute of the time previously set thus indicating that it is time to call.

If any of the four items above referred to occurs, then the light 206 is energized indicating that the system is in condition such that the telephone should not be used and the system goes to program step P1 or P4 depending upon which event occurred.

Program step P1 is the one minute warning time indicating that there is only one minute of recording time left until the timer causes the unit to call the monitor station. The busy check 210 system determines whether or not the telephone is being used and is thus busy. If the telephone is busy, a busy signal is provided to alert the telephone user that it is time that the telephone be cleared because the monitor station will be called within one minute. If the phone is busy then the system continues to provide the busy (beeper) sound and check to determine if the phone remains busy.

If, in fact, the phone continues to be utilized throughout the entire one minute period of time and is still busy at the expiration thereof, then at P2 the control logic module 200 through the dial switch (disconnect) 212 automatically disconnects and overrides the party using the telephone to permit dialing of the monitor station. This automatically occurs at the end of the time set by the timer 52.

Once the automatic dialing has occurred, the system checks to see if there is a connection to the monitor station at P3. If the monitor station is not connected to the phone line within the time limit (2 minutes) then the system goes automatically to P2 which again causes the system to dial the monitor station.

During program step P3 the real time ECG signals are connected by way of the telephone line to the monitor station. During this time a check is made by the patient's station for confirmation that it is, in fact, connected to the monitor station. If a confirmation signal from the monitor station has not been received, then a two minute time out sequence is established. If no confirmation signal is received during this two minute period then the system is reset to step P2 and the monitor station is again dialed. The confirmation by the monitor station, that it is, in fact on the line is transmission of a tone 1 or tone 3 timing signal to the system. Additionally, tone 1 may also be utilized for other purposes at different points in the program, such, for example, as breaking the connection at the end of a particular playback period thus stopping the playback of the prerecorded signal and allowing the telephone transmission to terminate.

Thus once the confirmation of the connection of the monitor station to the patient station has been received, whether during step P0 or P3, the unit then progresses to step P4. In step P4 the tone 1 received signal is cleared. In the event the patient has depressed the call button, such call button request is cleared. Thereafter, an identification code is applied from the control logic module 200 through the switch 224 into the amplifier 30 and it is recorded and also through switch 226 it is transmitted to the monitor to thereby identify the patient's station which is about to transmit the compressed signal. This code signal can also contain other digitally coded data, for example, the setting of the timer 52 and the total number of heartbeats since the last playback from the total counter 29.

At this stage the system progresses to P5 wherein the tape transport is caused to stop the movement of the recording tape. Thereafter, at P6, the tape is caused to rewind until the beginning of the tape (BOT) is received, at which point the system at P7 stops the rewinding of the tape. At P8 the playback of the prerecorded ECG signals in a compressed time mode is accomplished. This playback continues until the end of the tape is reached or a tone 1 or tone 3 signal is received at the patient's station. If any one of these three events occur the playback of the tape is stopped at P9. When the playback of the tape is stopped, the system progresses to P10 where the tape is rewound, to P11 where the rewinding of the tape is stopped, and subsequently to P12 where the system returns to the recording of the signals from the patient's telemetry transmitter in real time. Such continues again until the end of the tape has occurred or the timed period of recording has occurred if no tone 1 signal has been received from the monitor station. In the event such occurs, the system immediately returns to step P4 to again replay the information appearing on the tape. In the event a tone 1 is received at the conclusion of P12, such indicates that the monitor station has received the recorded signal and is completed with it and wishes the system to continue in its normal mode of recording and release the phone line until the next call occurs. If such occurs the system then goes to P13 which clears the tone 1, releases the recorder and causes the telephone to hang up when and if not in use by the patient talking with the monitor station. The system then returns to P0.

Tone 2 has its own specific program since it is a nonsynchronous type of activity and such is illustrated in FIG. 7 to which reference is hereby made. In the event the physician wishes to talk to the patient during a time when the system is in use, the monitor transmits a tone 2 signal to the patient's station. If a tone 2 signal occurs, such will first cause the system, through the control logic module, to clear tone 2 and to then determine whether or not the phone is busy by going through a phone busy check at 210. In the event the phone is busy, contact is established already so the ECG signals are immediately connected to the phone system so the physician may receive them. In the event the phone is not busy, then the audible and visual alarm 208 is activated, thus causing the patient to recognize that he should immediately pick up the phone to talk with the doctor or monitor technician. Under these circumstances, the doctor may be placed in direct communication with the patient.

Figure 8:
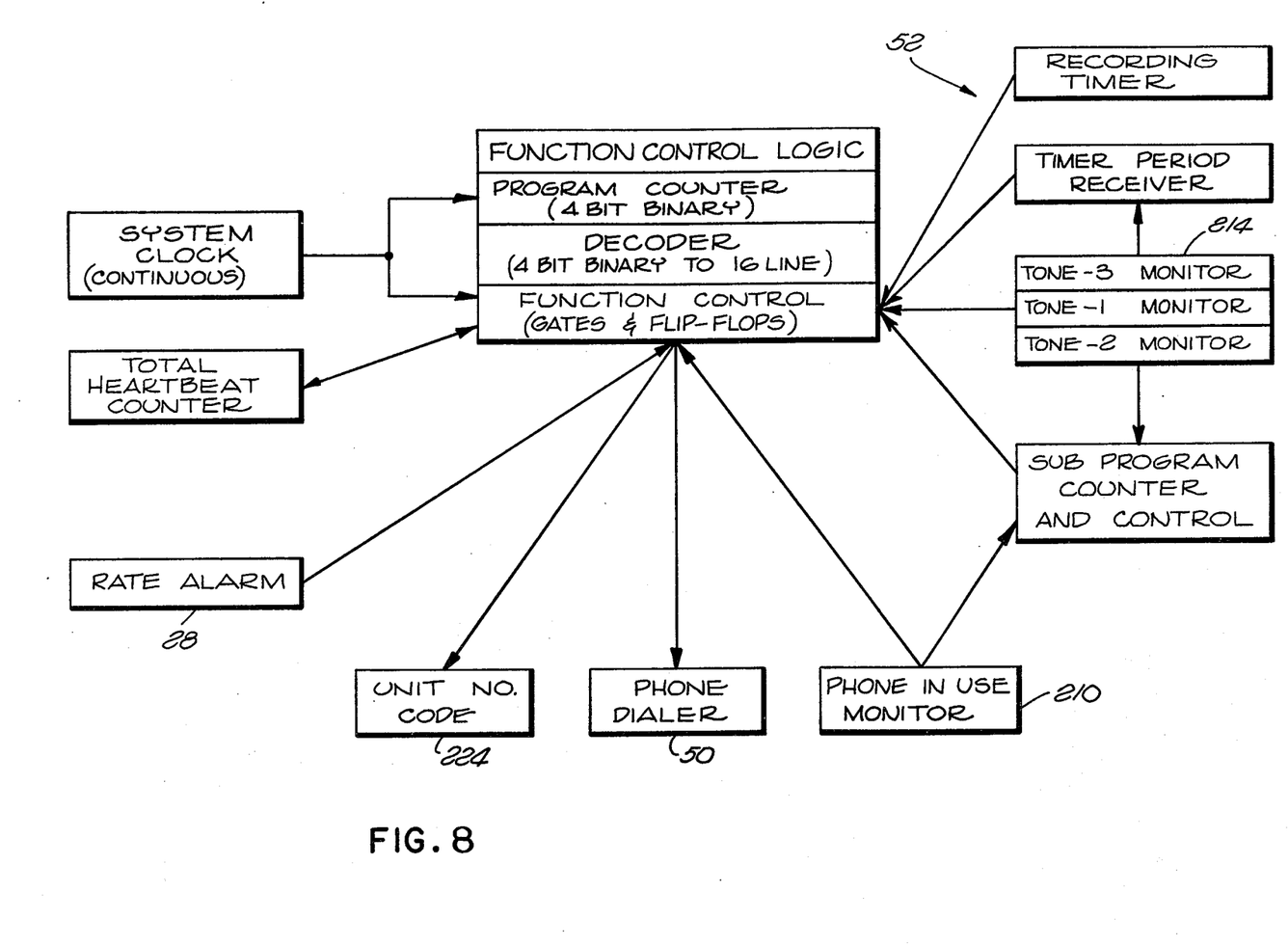
FIG. 8 is a generalized block diagram showing the control logic utilized in the system of the present invention.

As indicated in FIG. 8, to which reference is hereby made, the control logic module is a standard state-of-the-art system wherein a clock provides a continuous clock signal to the logic module. There is provided a program counter which is a standard 4 bit binary counter which then applies a signal to a decoder which is a standard 4 bit binary to 16 line decoder. The output of the decoder is applied to the function control system which includes standard gates and flipflops well known to those skilled in the art. The various functions above referred to are interconnected to the control logic module as is indicated by the various portions of the system and are identified by the same reference numerals. It is thus not believed that additional detailed description or discussion with respect to FIG. 8 is required.

From the foregoing it will now be recognized by those skilled in the art that during the normal sequence of operations of the continuous monitoring system constructed in accordance with the present invention, assuming that the recorder has been recording the patient's ECG signal in real time, the following events will occur. When the timer reaches the one minute warning time indicating that there is only one minute of recording time left, a busy signal is placed upon the phone line, if in fact the phone line is in use, thus providing a warning to the user that he should hang up the phone. At the same time, the call light becomes activated indicating that the telephone line is in use and should not be picked up. The timer then will go through the remaining one minute of recording time and reaches that position when the monitor station should be called. The unit automatically dials the monitor station and at the same point in time places the ECG signal on the line. The patient's station then waits for a period of up to two minutes for a confirmation signal from the monitor station, either tone 1 or tone 3 indicating that the monitor station has received the call and is ready itself to receive the compressed time playback electrocardiogram signals. The tone signals are carefully chosen so that they do not interfere with nor will they be responsive to the normal signals occurring in telephone use, for example, dial tone, ring tone, busy tone, or tones used for dialing. If the patient station does not receive the confirmation signal within this two minute period of time it then hangs up the telephone and automatically dials again. When the confirmation signal (tone 1 or tone 3) is received from the monitor station, then the identification code and other digitally coded data of the patient station is recorded on the tape and transmitted to the monitor station on the compressed time signal frequency (3000 Hz) where it is decoded and displayed. The recorder at this point in time stops, rewinds and plays back the recorded data at the compressed time as, for example, 20 times faster than the original recording time. The playback at this compressed time continues until the end of the tape is reached, unless during the playback a tone 1 or tone 3 signal is first received. Such a signal would normally be issued when the identifying code recorded in P4 is observed indicating the end of the latest recording has been reached.

Subsequent to the playback occurring, the recorder stops, rewinds and again starts recording the real time signal from the patient's telemetry transmitter. In the event a tone 1 or a tone 3 signal was received, it is echoed on the carrier of the 3000 hertz modulator along with the other digital data. Such a tone 3 signal is a timing data signal which establishes the time for recording of the real time data thus causing the system to cycle at any desired point in time. Such can be done by the physician or the technician at the monitor station, upon orders of the physician, in the event either more frequent monitoring or less frequent monitoring is required of this particular patient, without termination of the connection. In the event a tone 1 signal has been received, during or subsequent to the playback, the tape is rewound, recording commences, and then the patient's unit releases the phone line. If the patient is talking on the phone or the clear leader of the tape is still passing the record head, the real time data will continue to be transmitted over the phone line until such a time as the patient hangs up the phone and the tape is being recorded upon, thus permitting the appropriate operation to occur to thereby release the telephone line.

As above noted, the signal at the monitoring station may be utilized in various fashions. One of the utilizations is to apply the signal to a computer which has been properly programmed to analyze ECG signals. The computer accepts the time compressed data received from the patient's station, detects and quantitates total heartbeats and arrhythmias. The computer is programmed to quantitate the total number of supraventricular extrasystoles and the number of ventricular extrasystoles. It further clarifies the ventricular extrasystoles into single, paired, multiform and ventricular tachycardias. These classifications, as well as any others desired by the physician, of the significant warning arrhythmias and other data, allow comparison of the patient's progress on the periodic basis, for example, assuming that the patient's tape recorder is established for a one hour recording period then the patient's progress is compared on an hour by hour basis.

The technician attending the monitoring station should be a highly trained person, usually a coronary care nurse. This technician scans the information usually by reference to the oscilloscope or to the strip chart recorder which is providing a visual permanent record of the material which is being transmitted. At the same time, the technician would scan the computer readout. By analyzing the strip chart recording and the computer readout the technician would determine the need for continuing real time transmission of ECG signals currently being received at the monitoring station. If the need exists, the technician allows this transmission to continue by failing to transmit a tone 1 signal back to the patient station. If, however, the technician does not determine the requirement for a continuation of real time transmission of the ECG signals, then the monitor technician will provide a tone 1 signal to the patient's station thus causing the transmision to cease and the tape recorder to again commence recording the real time signals as above set forth.

Subsequent to receipt of the signal and the scanning thereof, the technician selects representative samples of any significant arrhythmia or electrocardiogram abnormality from the strip chart recording and combines these with the computer record, thus providing a periodic summary report of this particular patient. The summary report is sent by a telephone copying device to the physician who may be anywhere that is equipped with a telephone, e.g., his office, the hospital or his home. Obviously, the physician may be at the same site as the monitoring station, e.g., the coronary care unit and would directly receive the information. Upon receipt of the periodic report on his telephone copying apparatus, the physician is now in a position to scan the summary and determine what may be required insofar as additional treatment for this particular patient. It can thus be seen that a continuous and rapid monitoring of a patient occurs wherein ECG history is quickly analyzed and treatment varied as required. By way of example, utilizing a system as of the type above set forth, approximately three minutes is required for the telephone transmission from the patient to the monitoring station, assuming that a one hour tape has been rewound and played back. Four additional minutes is required for the computer to print out and the monitor technician to select arrhythmia samples. Typical telephone copying requires six minutes; thus the final summary report for the hour reaches the physician in 14 minutes following the transmission of the ECG information from the patient's station. If the tape recording is occurring on an hour by hour basis, the physician receives hourly reports of all heartbeats of the patient within 73 minutes at most from the time which they occur.

If the patient is being monitored on a 10 minute recording basis, then the heartbeats of the patient will get to the physician within 20 minutes of occurrence. It requires 10 minutes to record in real time, approximately 30 seconds for telephone transmission, 1 minute to analyze and recognize arrhythmias and 2 minutes to assemble the summary report. Thereafter the report is telephone copied in the required 6 minutes.

When the system continues in real time, that is, the real time signals are connected to the monitoring station, then reports are issued to the physician immediately where indicated. As also above noted, a tape recorder is in existence at the monitoring station and will receive all of the signals being transmitted whether compressed or real time and thus preserves a permanent record of those signals for future review should such be necessary.

By way of further examples to illustrate use of the present system, a typical patient treatment will now be given. If a patient has a large number of arrhythmias occurring, for example, more than 20 ectopic beats per hour then he will be continuously monitored in real time until the ectopic beats are controlled to the satisfaction of the physician. Also when a patient is first released to out-patient status, he will be monitored on a real time basis until the ectopic beats are in a condition satisfactory to the physician. Thereafter, the patient's ECG is recorded for short time periods (for example 10 minutes) and is then played back. If there are no arrhythmias detected during several playbacks, then the recording time is progressively extended, for example to 20 minutes, then 40 minutes, and then 60 minutes. Thereafter the patient's ECG is followed for 60 minute intervals.

In the event the scan discloses arrhythmias have occurred, then the monitor technician changes the review period to such shorter time as the physician prescribes. Of course, after each monitor period a summary report is provided the physician with particular emphasis on any arrhythmias noted.

Figure 9:
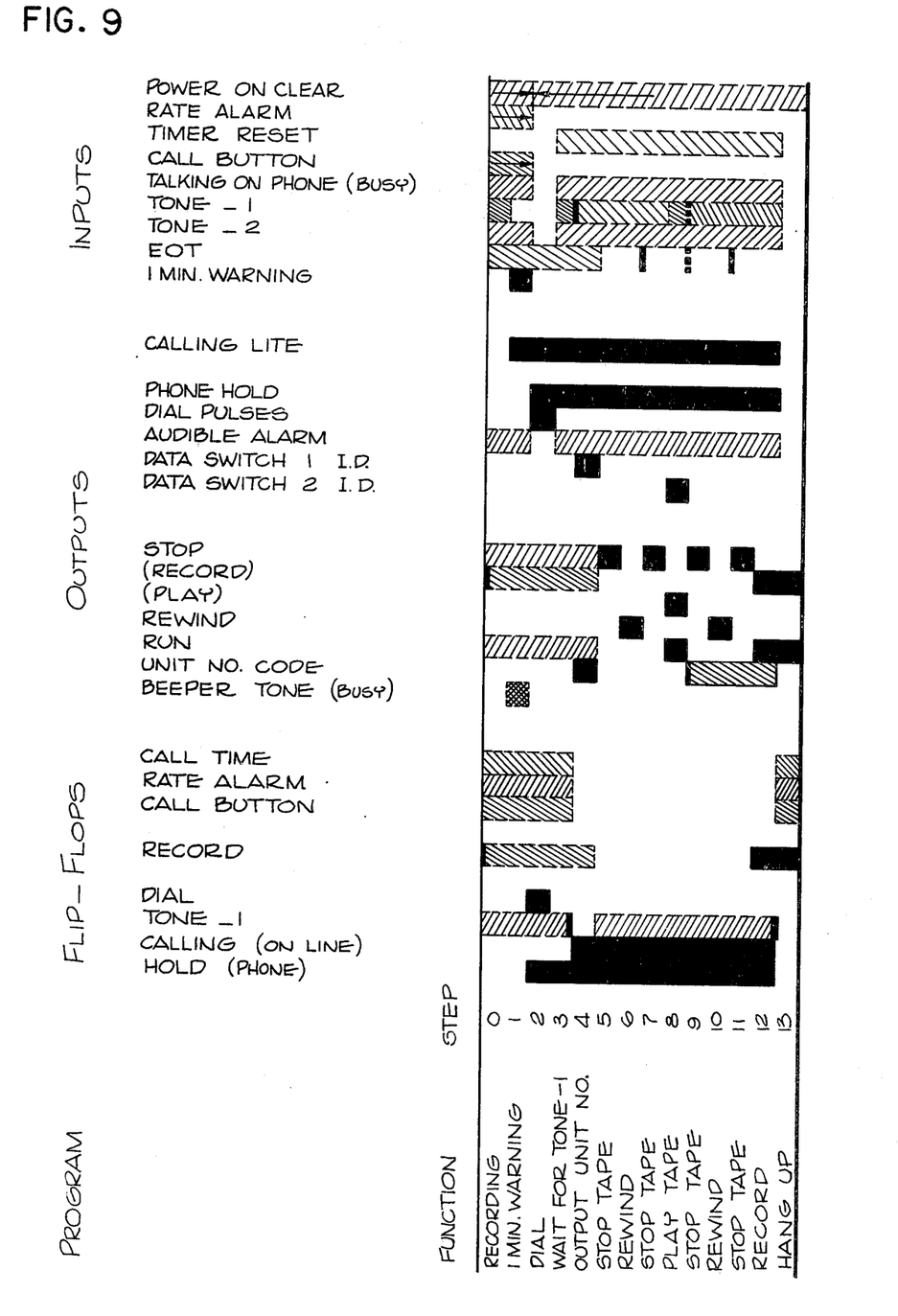
FIG. 9 is a timing diagram illustrative of the time during which various signals may occur throughout the functioning of the system constructed in accordance with the present invention.

Reference is now made to FIG. 9 which provides a timing diagram that correlates the various inputs, outputs and logic functions with the particular step P0 through P13 in the program for the patient's station. The various portions of the bar graph utilize the code wherein if the area following the input-output or flip-flop is cross hatched, it means the particular signal indicated may occur during that particular point in time. If it is completely clear it means that it cannot occur during that particular time. If it is solid, it means that the particular input-output or flip-flop is activated during that particular point in time. Thus, for example, the calling light is on throughout function steps P1 through P12 while, on the other hand, the one minute warning input is on only during function step P1, that is, the one minute warning function step. As an additional example to assist in reading the timing chart the stop signal which causes the tape to stop will occur always in function steps P5, P7, P9 and P11 and may occur during steps P0 through P4 depending upon whether an end of tape (EOT) signal is received. As would be anticipated from the foregoing discussion, the rate-rhythm alarm is on at all times when the patient's unit is not connected to the monitor station P0 and thus may be activated as a result of abnormal bradycardia or tachycardia. It is believed that with the foregoing explanation and by reference to the flow charts, FIGS. 5, 6 and 7, that the timing diagram will be self-evident and thus additional discussion thereof is not required herein.

Figure 10:
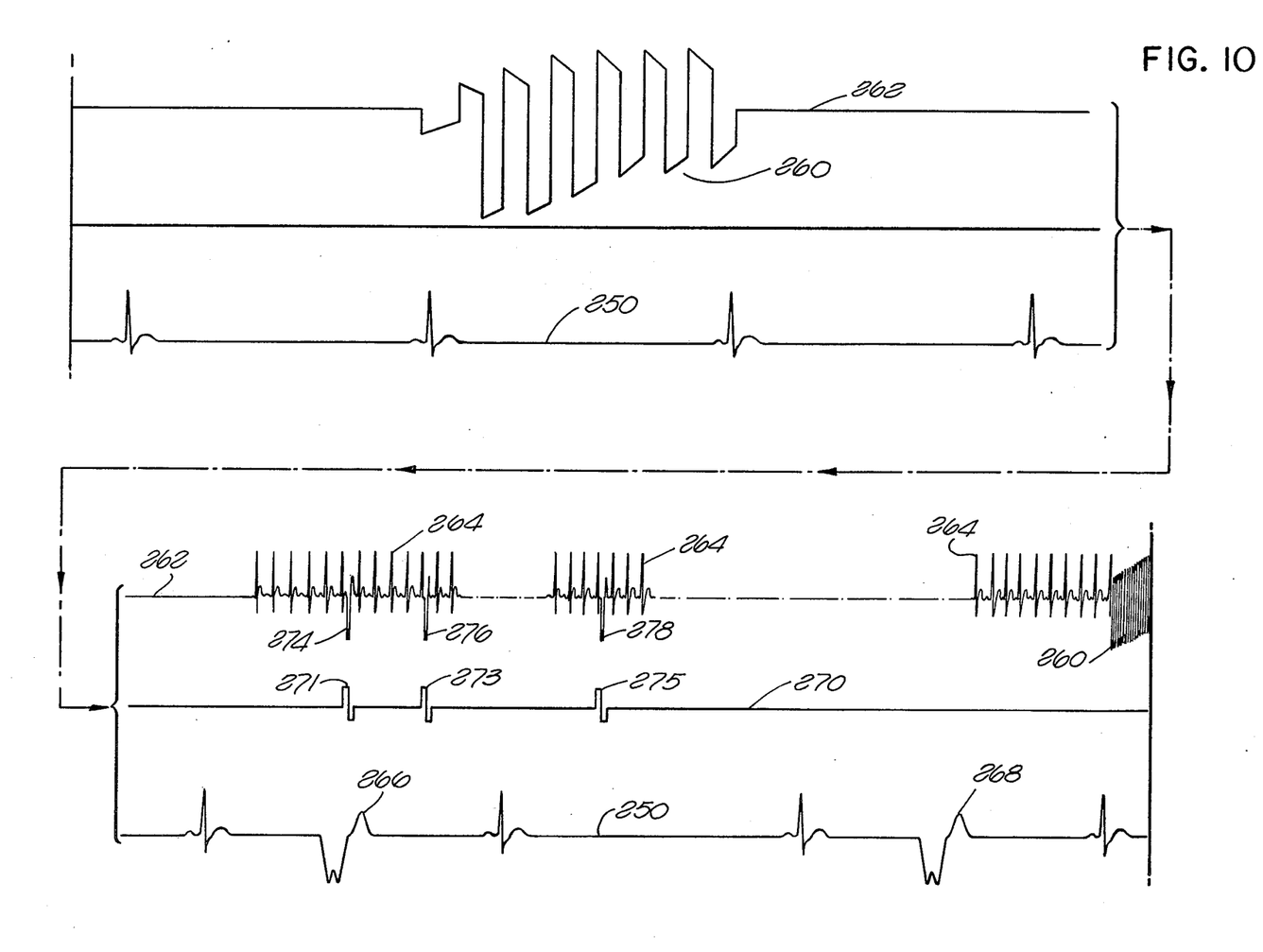
FIG. 10 is a graph illustrating a typical electrocardiogram signal wave form recorded by the monitoring station portion of the system constructed in accordance with the present invention.

Reference is now made to FIG. 10 which represents a typical strip chart recording made utilizing a system constructed in accordance with the principles of the present invention. As is therein shown the graph at 250 represents the real time patient's ECG signal being received and recorded at the monitor station. Such, of course, would occur during all periods of time that the monitor station is connected, including times when the tape recorder is not recording the signal being received.

As will be recalled from the foregoing discussion, when the end of the tape occurs with the system connected or the confirmation signal is first received from the monitoring station, an identification code is first transmitted and such is as illustrated at 260 in FIG. 10. The tape recorder ceases recording the patient's heartbeat at the commencement of the identification code, however, the monitor station is now recording the ECG signal while the identification code is transmitting in real time to the monitoring station and simultaneously therewith is recorded on the tape at the patient's station at the end of the patient's signal recording time. Subsequent to receipt and recordation of the patient's identification signal or code, the tape transport commences the rewind of the tape and such is illustrated at 262 on FIG. 10. At the conclusion of the rewind time the tape recorder commences to play back the prerecorded signal at a compressed time, and in accordance with the preferred embodiment, at 20 times the previously recorded rate. Such compressed playback signal is shown at 264 in FIG. 10. It will be noted that throughout this entire period of time the signal 250 has continued to be recorded. At the conclusion of the 20 times recorded signal playback, the identification code 260 is again played back but at this point in time at 20 times its previously recorded rate. Such playback of the identification code indicates the termination of the recording of the most recently recorded signal.

As is illustrated in FIG. 10, during the time compressed playback of the ECG recording the patient may experience an arrhythmia which will be immediately detected. For example premature ventricular extrasystoles occur at 266 and 268 on the real time tracing 250. Alternatively, these arrhythmias may have occurred during the prerecorded ECG and would be detected both in the rate-rhythm curve 270 as shown at 271, 273 and 275 and by scanning the compressed ECG 264 where the ventricular extrasystoles are depicted at 274, 276, and 278. Upon such detection that part of the ECG would be expanded and provided to the physician as part of the summary report.

From the foregoing it can be seen that a complete record of a cardiac patient's ECG signals is maintained and transmitted to a central monitoring station where a permanent record is maintained and the electrocardiogram material is properly analyzed. Such analysis enables a trained person to ascertain whether arrhythmias are occurring and if so, whether they are such as to lead to ventricular fibrillation. In addition thereto, appropriate quantification of arrhythmias occurs and this has prognostic value. In the event 20 or more ventricular extrasystoles per hour occur, such is a definite warning sign and in cardiac patients is associated with a higher probablity of sudden death. The rhythm, of course, must be monitored for the full 24 hours to objectively quantitate all the arrhythmias that occur during the day and night. In addition to identification thereto by having the electrocardiogram signal available for monitoring, the configuration of the electrocardiogram complex itself may be obtained. That is, the QRS and ST segments of the electrocardiogram signal may reflect the degree of ischemia, that is, blood supplied to the heart. Thus, elevation or depression of the ST segment of the electrocardiogram may suggest certain diagnosis as the etiology. This deviation of the ST segment can occur without associated arrhythmias and, of itself, be of great importance.

What is claimed is:

1. System for providing cardiac information from a cardiac patient to a remote station comprising:

means for recording electrocardiogram signals produced by the patient in real time at a first predetermined rate;

means for reproducing said recorded signals at a second predetermined rate, said second predetermined rate being greater than said first predetermined rate thereby compressing the time required to reproduce said signals as compared to the time to record said signals;

means for monitoring said reproduced signals;

a communication interface which includes a telephone system having direct dialing capability coupling said reproducing means to said monitoring means;

an automatic telephone dialing means coupled to said telephone system; and timer means, said timer means activating said automatic dialing means for controlling the periodicity of transmission of recorded signals from said recording means to said monitoring means.

2. A system as defined in claim 1 wherein said means for recording includes a transmitter means for attachment to the patient and receiver means tuned to receive signals transmitted by said transmitter means which signals are representative of electrocardiogram signals from said patient.

3. A system as defined in claim 2 wherein said means for recording further includes modulator means for frequency modulating a carrier having a first frequency responsive to variations in said received signals representative of said electrocardiogram signals.

4. A system as defined in claim 3 wherein said means for recording further includes a magnetic tape recording medium upon which said frequency modulated signals are recorded as said tape moves at a first predetermined speed and are reproduced as said tape moves at a second predetermined speed, said second speed being faster than said first speed.

5. A system as defined in claim 4 wherein said reproducing means includes a demodulator means having a carrier having a second frequency, said second frequency being greater than said first frequency by an amount proportional to the difference between said first and second speeds.

6. A system as defined in claim 1 wherein said timer means includes means for changing the timer at said recording means and at said monitoring means.

7. A system as defined in claim 1 which further includes means for detecting a variation in the repetition rate of said electrocardiogram signals beyond predetermined limits and automatically establishing a communication with said monitoring means responsive thereto.

8. A system as defined in claim 1 which further includes means for detecting a variation in the rhythm of said electrocardiogram signals beyond predetermined limits and automatically establishing a communication with said monitoring means responsive thereto.

9. A system as defined in claim 1 which further includes means for detecting a variation in the repetition rate and the rhythm of said electrocardiogram signals beyond predetermined limits and automatically establishing a communication with said monitoring means responsive thereto.

10. A system as defined in claim 1 which further includes means for detecting a variation in the repetition rate of said electrocardiogram signals beyond predetermined limits and providing an output signal responsive thereto, and means for connecting said output signal to said automatic dialing means for establishing communication with said monitoring means.

11. A system as defined in claim 1 which further includes means for detecting a variation in the rhythm of said electrocardiogram signals beyond predetermined limits and providing an output signal responsive thereto, and means for connecting said output signal to said automatic dialing means for establishing communication with said monitoring means.

12. A system as defined in claim 1 which further includes means for detecting a variation in the repetition rate and the rhythm of said electrocardiogram signals beyond predetermined limits and providing an output signal responsive thereto, and means for connecting said output signal to said automatic dialing means for establishing communication with said monitoring means.

13. A system as defined in claim 1 which further includes means for simultaneously transmitting said electrocardiogram signals in real time to said monitoring means with said reproduced signals.

14. A system as defined in claim 13 which further includes, at said monitoring means, means for making a record of said reproduced and real time electrocardiogram signals.

15. A system as defined in claim 14 wherein said means for making a record is a strip chart recorder.

16. A system as defined in claim 14 which further includes means for communication with a physician including a communication interface with said monitoring means and a communication interface with said patient.

17. A system as defined in claim 16 which further includes means for alerting said patient to communicate verbally with said monitoring means or said physician.

18. A system as defined in claim 1 which further includes indicator means for providing an indication to said patient that said system is producing said signals and providing said signals to said means for monitoring.

19. A system as defined in claim 1 which further includes indicator means for providing an identification of said patient to said monitoring means.

20. A system as defined in claim 1 which further includes means for totalizing said patient's heartbeats and transmitting said total to said monitoring means.

21. A system as defined in claim 1 wherein said automatic dialing means, once activated, continues to automatically dial said monitoring means until communication therewith is established.

22. A system as defined in claim 1 which further includes means manually operable by said patient for activating said telephone communication interface thereby to connect said signals to said monitoring means upon demand of said patient.

23. A system as defined in claim 1 wherein said means for monitoring further includes means for generating a confirmation signal responsive to coupling of said reproducing means to said monitoring means and means for transmitting said confirmation signal over said telephone communication interface to said reproducing means, said reproducing means transmitting said signals to said monitoring means only in response to receiving said confirmation signal.

24. A system as defined in claim 1 wherein said means for monitoring includes means for automatically analyzing said signals and displaying appropriate information with respect thereto.

25. Method for providing cardiac information from a cardiac patient to a remote station comprising:
   recording the electrocardiogram signals produced by the patient in real time at a first predetermined rate;
   reproducing said recorded signals at a second predetermined rate, said second predetermined rate being greater than said first predetermined rate thereby compressing the time required to reproduce said signals as compared to the time to record said signals;
   automatically dialing a telephone to connect said reproduced signals to a station remote from said patient;
   transmitting said reproduced signals by said telephone to said station remote from said patient;
   analyzing said reproduced signals; and
   varying the periodicity of transmission of said reproduced signals responsive to said analysis.

26. A method as defined in claim 25 which further comprises the step of simultaneously transmitting the real time electrocardiogram signals along with said reproduced signals on said telephone to said remote station.

27. System for providing cardiac information from a cardiac patient to a remote station comprising:
   means for recording electrocardiogram signals produced by the patient in real time at a first predetermined rate;
   means for reproducing said recorded signals at a second predetermined rate, said second predetermined rate being greater than said first predetermined rate thereby compressing the time required to reproduce said signals as compared to the time to record said signals;
   means for monitoring said reproduced signals;
   a communication interface which includes a telephone system having direct dialing capability coupling said reproducing means to said monitoring means;
   an automatic telephone dialing means coupled to said telephone system; and
   means manually operable by said patient for activating said telephone communication interface thereby to connect said signals to said monitoring means upon demand of said patient.

28. A system as defined in claim 27 wherein said means for recording includes a transmitter means for attachment to the patient and receiver means tuned to receive signals transmitted by said transmitter means which signals are representative of electrocardiogram signals from said patient.

29. A system as defined in claim 28 which further includes means for detecting a variation in the repetition rate and the rhythm of said electrocardiogram signals beyond predetermined limits and automatically establishing, through said telephone, a communication with said monitoring means responsive thereto.

30. A system as defined in claim 27 wherein said means for monitoring includes means for automatically analyzing said signals and displaying appropriate information with respect thereto.

31. A system as defined in claim 27 which further includes means for detecting a variation in the repetition rate and the rhythm of said electrocardiogram signals beyond predetermined limits and automatically establishing, through said telephone, a communication with said monitoring means responsive to occurrence of said variation in either said repetition rate or said rhythm.

32. A system as defined in claim 27 which further includes means for simultaneously transmitting said electrocardiogram signals in real time to said monitoring means with said reproduced signals.

33. A system as defined in claim 32 which further includes, at said monitoring means, means for making a record of said reproduced and real time electrocardiogram signals.

34. A system as defined in claim 33 which further includes means for communication with a physician including a communication interface with said monitoring means and a communication interface with said patient.

35. A system as defined in claim 34 which further includes means for alerting said patient to communicate verbally with said monitoring means or said physician.

36. A system as defined in claim 27 which further includes indicator means for providing an identification of said patient to said monitoring means.

37. A system as defined in claim 27 wherein said automatic dialing means, once activated, continues to automatically dial said monitoring means until communication therewith is established.

38. A system as defined in claim 27 wherein said means for monitoring further includes means for generating a confirmation signal after activation of said communication interface thereby enabling coupling of said reproducing means to said monitoring means and means for transmitting said confirmation signal over said telephone communication interface to said reproducing means, said reproducing means transmitting said signals to said monitoring means in response to receiving said confirmation signal.

* * * * *